(12) United States Patent
Miralles et al.

(10) Patent No.: US 11,958,945 B2
(45) Date of Patent: Apr. 16, 2024

(54) DILUTABLE DISPERSIONS

(71) Applicant: ECOLAB USA INC., Saint Paul, MN (US)

(72) Inventors: Altony J. Miralles, Saint Paul, MN (US); Claire Lucille Notermann, Saint Paul, MN (US)

(73) Assignee: ECOLAB USA INC., Saint Paul, MN (US)

( * ) Notice: Subject to any disclaimer, the term of this patent is extended or adjusted under 35 U.S.C. 154(b) by 640 days.

(21) Appl. No.: 16/727,509

(22) Filed: Dec. 26, 2019

(65) Prior Publication Data

US 2020/0207926 A1 Jul. 2, 2020

Related U.S. Application Data

(60) Provisional application No. 62/786,150, filed on Dec. 28, 2018.

(51) Int. Cl.
| | | |
|---|---|---|
| *C08J 3/07* | (2006.01) | |
| *C08F 220/14* | (2006.01) | |
| *C08L 33/08* | (2006.01) | |
| *C08L 33/10* | (2006.01) | |

(52) U.S. Cl.
CPC .............. *C08J 3/07* (2013.01); *C08F 220/14* (2013.01); *C08L 33/08* (2013.01); *C08L 33/10* (2013.01)

(58) Field of Classification Search
CPC ........... C08J 3/07; C08F 220/14; C08L 33/08; C08L 33/10
See application file for complete search history.

(56) References Cited

U.S. PATENT DOCUMENTS

| | | | | |
|---|---|---|---|---|
| 6,238,646 | B1 * | 5/2001 | Zembrodt | A61K 9/008 424/DIG. 10 |
| 2007/0010607 | A1 | 1/2007 | Smith et al. | |
| 2007/0275867 | A1 * | 11/2007 | Serobian | C09G 1/16 510/466 |
| 2008/0153736 | A1 * | 6/2008 | Elder | A61Q 13/00 512/4 |
| 2012/0058060 | A1 * | 3/2012 | Noor | A61K 8/34 526/292.9 |
| 2017/0246097 | A1 * | 8/2017 | Calvert | A61K 8/19 |

FOREIGN PATENT DOCUMENTS

| | | |
|---|---|---|
| EP | 1219288 A2 | 3/2002 |
| EP | 2455063 A1 | 5/2012 |
| WO | 02077150 A1 | 10/2002 |
| WO | 2010123865 A2 | 10/2010 |

\* cited by examiner

*Primary Examiner* — James C Goloboy
(74) *Attorney, Agent, or Firm* — McKee, Voorhees & Sease, PLC (57) ABSTRACT

Low concentration surfactant emulsions and methods of making and using the same are disclosed herein. The emulsions have the benefit of employing less surfactant than conventional emulsions. Further, the emulsions are dilutable and retain their stability upon dilution. A benefit of the emulsions is that they leave a low residue, preferably no residue, on a surface after contact.

15 Claims, 3 Drawing Sheets

FIGURE 1A

| Component | | | | | | | | | | | | | | | | | | | | | | | | | | | |
|---|---|---|---|---|---|---|---|---|---|---|---|---|---|---|---|---|---|---|---|---|---|---|---|---|---|---|---|
| Neodol 25-12 | 1 | 1 | 1 | 1 | 1 | 1 | 1 | 1 | | | | | | | | | | | | | | | | | | | | |
| Tomadol 25-7 | | | | | | | | | 1 | | | | | | | | | | | | | | | | | | | |
| Tomamine E-14-2 | | | | | | | | | | 1 | 1 | 1 | | | | | | | | | | | | | | | | |
| Tomamine Q-14-2 (75%) | | | | | | | | | | | | | 1.33 | 1.33 | 1.33 | 1.33 | | | | | | | | | | | | |
| Tomamine Q-C-15 | | | | | | | | | | | | | | | | | | | | | 1 | 1 | 1 | | | | | |
| Tomadol 901 | | | | | | | | | | | | | | | | | | | | 1 | 1 | 1 | 1 | | | | | |
| Tomadol 902 | | | | | | | | | | | | | | | | | | | | | | | | | 1 | | | |
| Hampsyl L | | | | | | | | | | | | | | | | | | | | | | | | 1 | 1 | 0.5 | 0.5 | |
| Hampsyl M (30%) | | | | | | | | | | | | | | | | | | | | | | | | | | | | |
| Glucopon | | | | | | | | | | | | | | | | | | | | | | | | | | | | |
| Amphosol CA | | | | | | | | | | | | | | | | | | | | | | | | | | | | |
| SLS Powder | | | | | | | | | | | | | | | | | | | | | | | | | | | | |
| Aromox C/12W | | | | | | | | | | | | | | | | | | | | | | | | | | | | |
| Berol R648 | | | | | | | | | | | | | | | | | | | | | | | | | | | | |
| Sodium Stearate | | | | | | | | | | | | | | | | | | | | | | | | | | | | |
| Pemulen 1622 | 0.6 | 0.6 | 0.6 | 0.6 | 0.6 | 0.6 | 0.6 | 0.6 | 0.6 | 0.6 | 0.6 | 0.6 | 0.6 | 0.6 | 0.6 | 0.6 | 0.6 | 0.5 | 0.6 | 0.6 | 0.6 | 0.6 | 0.6 | 0.6 | 0.6 | 0.6 | 0.6 | 0.5 |
| Mineral Oil | 10 | 10 | 10 | 10 | 10 | 10 | 50 | 25 | 10 | 10 | 10 | 10 | 10 | 10 | 10 | 10 | 10 | 10 | 10 | 10 | 10 | 10 | 10 | 10 | 10 | 10 | 10 | 10 |
| DI Water | 88.4 | 87.3 | 87.3 | 87.4 | 87.2 | 86.7 | 41 | 66 | | 86.7 | 87.2 | 88.2 | 87.87 | 87.67 | 87.57 | | 87.2 | 88.2 | | 86.7 | 85.7 | | | 87.2 | | | | |
| Soft Water | | | | | | | | | 88.2 | 88.2 | | | | | | 87.57 | | | 88.2 | | | 87.2 | 87.2 | | | 88.2 | 88.7 | 88.8 |
| 5 grain Water | | | | | | | | | | | | | | | | | | | 88.2 | | | 85.7 | | | | | | |
| NaOH | 0.2 | 0.2 | 0.2 | 0.2 | 0.2 | 0.2 | 1 | 1 | 0.2 | 0.2 | 0.2 | 0.2 | 0.2 | 0.4 | 0.5 | 0.5 | 0.2 | 0.2 | 0.2 | 0.2 | 0.2 | 0.2 | 0.2 | 0.2 | 0.2 | 0.2 | 0.2 | 0.2 |
| NaCl | | | | 1.5 | | | 1.5 | 1 | | | | | | | | | 1 | | | 1.5 | 2.5 | 2.5 | 1 | 1 | 1 | | | |
| Sodium Polyacrylate | | 1 | 1 | | | | | | | | | | | | | | | | | | | | | | | | | |
| pH | ~7 | ~7 | ~7 | ~7 | ~7 | ~7 | ~7 | ~7 | ~7 | ~7 | ~7 | ~7 | ~7 | ~7 | ~7 | ~7 | ~7 | ~7 | ~7 | ~7 | ~7 | ~7 | ~7 | 5 | 5 | ~7 | ~7 | ~7 |

*FIGURE 1A*

| Component | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Neodol 25-12 | | | | | | | | | | | | | | |
| Tomadol 25-7 | | | | | | | | | | | | | | |
| Tomamine E-14-2 | | | | | | | | | | | | | | |
| Tomamine Q-14-2 (75%) | | | | | | | | | | | | | | |
| Tomamine Q-C-15 | | | | | | | | | | | | | | |
| Tomadol 901 | | | | | | | | | | | | | | |
| Tomadol 902 | | | | | | | | | | | | | | |
| Hamposyl L | 0.7 | 0.8 | 0.8 | | | | | | | | | | | |
| Hamposyl M (30%) | | | | 3.33 | | | | | | | | | | |
| Glucopon | | | | 2 | | | | | | | | | | |
| Amphosol CA | | | | | 3.33 | 1.67 | 0.83 | | | | | | | |
| SLS Powder | | | | | | | | 1 | | | | | | |
| Aromox C/12W | | | | | | | | | 3.33 | | | | | |
| Berol R648 | | | | | | | | | | 1 | | | | |
| Sodium Stearate | | | | | | | | | | | | 0.5 | 0.5 | 0.5 |
| Pemulen 1622 | 0.5 | 0.5 | 0.49 | 0.6 | 0.6 | 0.6 | 0.6 | 0.6 | 0.6 | 0.6 | 0.6 | 0.6 | 0.6 | 0.6 |
| Mineral Oil | 10 | 10 | 10 | 10 | 10 | 10 | 10 | 10 | 10 | 10 | 10 | 10 | 10 | 10 |
| DI Water | | | | | 83.2 | 87.2 | 87.03 | 87.87 | 87.2 | 84.87 | 87.2 | | | |
| Soft Water | 88.6 | 88.5 | 88.6 | 85.9 | | | | | | | | 88.7 | 88.7 | 88.7 |
| 5 grain Water | | | | | | | | | | | | | | |
| NaOH | 0.2 | 0.2 | 0.2 | 0.2 | 0.2 | 0.2 | 0.2 | 0.2 | 0.2 | 0.2 | 0.2 | 0.2 | 0.2 | 0.2 |
| NaCl | | | | | 1 | 0.5 | 0.5 | 1 | 1 | 1 | 1 | | | |
| Sodium Polyacrylate | | | | 4 | | | | | | | | | | |
| pH | ~7 | ~7 | ~7 | ~7 | ~7 | ~7 | ~7 | ~7 | ~7 | ~7 | ~7 | ~7 | ~7 | ~7 |

*FIGURE 1B*

| Pemulen 1621 | Mineral Oil | Neodol 25-12 | Glucopon 625 | Calfax 6LA-70 | Hamposyl C (97%) | SLES (60%) | Berol R648 | SLS Powder | Sodium Acrylate | NaCL (20%) | NaOH (50%) | Results |
|---|---|---|---|---|---|---|---|---|---|---|---|---|
| 0.5 | 10 | 1 | | | | | | | | | 0.2 | Unstable |
| 0.5 | 10 | 1.5 | | | | | | | | | 0.3 | Unstable |
| 0.5 | 10 | 1 | | | | | | | 0.73 | | 0.3 | Unstable |
| 0.5 | 10 | 1 | | | | | | | 1.56 | | 0.2 | Unstable |
| 0.5 | 10 | 1 | | | | | | | 4.4 | | 0.4 | Unstable |
| 0.9 | 10 | 1 | | | | | | | | 2 | 0.2 | Unstable |
| 0.9 | 10 | 1 | | | | | | | | 1 | 0.2 | Stable |
| 0.9 | 10 | | | | | | | | | 1.5 | 0.2 | Unstable |
| 0.9 | 10 | | 2 | | | | | | 3.2 | | 0.2 | Stable |
| 0.9 | 10 | | 2 | | | | | | 7.73 | | 0.2 | Unstable |
| 0.9 | 10 | | 2 | | | | | | | 0.8 | | Unstable |
| 0.9 | 10 | | | 3.5 | 1 | | | | | 1 | 0.2 | Stable |
| 0.9 | 10 | | | | 0.5 | | | | | 3 | 0.2 | Stable |
| 0.9 | 10 | | | | 0.25 | | | | | 2.5 | 0.2 | Stable |
| 0.9 | 10 | | | | 0.25 | | | | | 2.5 | 0.2 | Stable |
| 0.9 | 10 | | | | | 1.67 | | | 3 | 2 | 0.2 | Unstable |
| 0.9 | 10 | | | | | | 1.67 | | | 2 | 0.4 | Unstable |
| 0.9 | 10 | | | | | | 0.84 | | | | 1.65 | Unstable |
| 0.9 | 10 | | | | | | 0.42 | | | 2.2 | 0.8 | Unstable |
| 0.9 | 10 | | | | | | | 1 | | 3 | 0.33 | Unstable |

*FIGURE 2*

DILUTABLE DISPERSIONS

CROSS REFERENCE

This application claims priority under 35 U.S.C. § 119 to provisional application U.S. Ser. No. 62/786,150 filed on Dec. 28, 2019 entitled "DILUTABLE DISPERSIONS", which is herein incorporated by reference in its entirety.

TECHNICAL FIELD

The disclosure relates stable dilutable dispersions. In particular, the disclosure relates to low surfactant emulsions in stable dilutable dispersions.

TECHNICAL BACKGROUND

Emulsions provide the ability to combine otherwise immiscible materials in a single composition by separating the incompatible ingredients from each other and one soluble by encapsulating it within a soluble dispersion, i.e., an emulsion. In doing so, one can provide an ingredient within a composition in which it is incompatible. There have been limitations in the use of emulsion though due to the need to include higher concentrations of emulsifying surfactants. Further, these surfactants have resulted in residues being left on surfaces that the emulsions contact. This has limited the use of emulsions in many types of compositions. Additionally, emulsions have not typically been dilutable without comprising their stability, particularly over time.

Thus, there is a need to provide compositions containing emulsions which are improved.

Accordingly, it is an objective of the claimed invention to provide compositions comprising emulsions which are dilutable and retain stability upon dilution.

A further object of the invention is to provide compositions comprising emulsions which do not leave residues on surfaces.

A further object of the invention is to provide compositions comprising emulsions which lower surfactant concentrations.

Other objects, advantages and features of the present invention will become apparent from the following specification taken in conjunction with the accompanying figures.

BRIEF SUMMARY

An advantage of the invention is that the compositions comprising emulsions are dilutable and the emulsions retain their stability upon dilution. It is an advantage of the present invention that the concentration of surfactant forming the emulsion can be greatly reduced compared to traditional emulsions. Further the compositions comprising the emulsions described herein leave little, or preferably no, residue on surfaces after contact.

A preferred embodiment is a composition comprising a carrier and an emulsion comprising a surfactant, wherein the surfactant forms an interfacial film; wherein the surfactant comprises between about 0.01 wt. % and about 1 wt. % of the composition; wherein the surfactant comprises a copolymer comprising acrylic acid, and wherein the surfactant has an HLB of at least about 6; and wherein the emulsion is stable at temperatures between about 10 and about 40° C. and stable upon dilution within the composition.

Another preferred embodiment is a composition comprising a carrier and an emulsion comprising a surfactant, wherein the carrier comprises water, a solvent, or a mixture thereof; wherein the surfactant forms an interfacial film; wherein the surfactant comprises between about 0.1 wt. % and about 1 wt. % of the composition; wherein the carrier comprises between about 95 wt. % and about 98 wt. % of the composition; wherein the surfactant comprises a crosslinked copolymer of acrylic acid and a C10-C30 alkyl acrylate, and wherein the surfactant has an HLB of at least about 7; wherein the emulsion is stable at temperatures between about 10° C. and about 40° C. and stable upon dilution within the composition.

Preferably, the compositions can be diluted at a ratio between about 1:2 and about 1:25 of emulsion to carrier. Still in another embodiment, the emulsion can further comprise a chelating agent, a thickener, an additional surfactant, or a mixture thereof. In a preferred embodiment, the emulsion encapsulates a hydrophobic component, a fragrance, a dye, an encapsulated surfactant, water, or a mixture thereof.

A preferred embodiment is also a method of diluting an emulsion comprising obtaining an emulsion comprising a surfactant and a first carrier; wherein the first carrier comprises water, a solvent, or a mixture thereof; wherein the surfactant forms an interfacial film; wherein the surfactant comprises a copolymer comprising acrylic acid; wherein the surfactant has an HLB of at least about 6; diluting the emulsion with a second carrier to form a diluted composition; wherein the second carrier is water, a solvent, or a mixture thereof; wherein the emulsion is diluted at a ratio of emulsion to second carrier of between about 1:2 and about 1:25; wherein upon dilution the surfactant has a concentration of between about 0.01 wt. % and about 0.5 wt. % of the diluted composition; wherein the concentration of the first carrier and second carrier combined are between about 95 wt. % and about 99 wt. %; wherein the emulsion in the diluted composition is stable at temperatures between about 10° C. and about 40° C. and for at least 24 hours.

While multiple embodiments are disclosed, still other embodiments of the present invention will become apparent to those skilled in the art from the following detailed description, which shows and describes illustrative embodiments of the invention.

Accordingly, the figures and detailed description are to be regarded as illustrative in nature and not restrictive.

BRIEF DESCRIPTION OF THE FIGURES

FIGS. 1A and 1B show experimental details for Pemulen 1622 polymer with various surfactants from Example 2.

FIG. 2 shows experimental details for Pemulen 1621 polymer with various surfactants from Example 2.

Various embodiments of the present invention will be described in detail with reference to the drawings. Reference to various embodiments does not limit the scope of the invention. Figures represented herein are not limitations to the various embodiments according to the invention and are presented for exemplary illustration of the invention.

DETAILED DESCRIPTION OF THE PREFERRED EMBODIMENTS

The present application relates to compositions comprising dispersions (emulsions). The emulsions have many advantages over conventional emulsions. For example, the emulsions described herein are dilutable and retain their emulsified state even during and after dilution in the composition. Further, the emulsions leave little, or even no, residue on a surface after contact. The embodiments of this invention are not limited to particular cleaning compositions, which can vary and are understood by skilled artisans.

It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers defining the range and include each integer within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4% This applies regardless of the breadth of the range.

Definitions

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring techniques and equipment, with respect to any quantifiable variable, including, but not limited to, mass, volume, time, temperature, pH and the like. Further, given solid and liquid handling procedures used in the real world, there is certain inadvertent error and variation that is likely through differences in the manufacture, source, or purity of the ingredients used to make the compositions or carry out the methods and the like. The term "about" also encompasses amounts that differ due to different equilibrium conditions for a composition resulting from a particular initial mixture. The term "about" also encompasses these variations. Whether or not modified by the term "about," the claims include equivalents to the quantities.

As used herein, the term "analog" means a molecular derivative of a molecule. The term is synonymous with the terms "structural analog" or "chemical analog."

As used herein, the term "oligomer" refers to a molecular complex comprised of between one and ten monomeric units. For example, dimers, trimers, and tetramers are considered oligomers. Furthermore, unless otherwise specifically limited, the term "oligomer" shall include all possible isomeric configurations of the molecule, including, but are not limited to isotactic, syndiotactic and random symmetries, and combinations thereof. Furthermore, unless otherwise specifically limited, the term "oligomer" shall include all possible geometrical configurations of the molecule.

As used herein the term "polymer" refers to a molecular complex comprised of a more than ten monomeric units and generally includes, but is not limited to, homopolymers, copolymers, such as for example, block, graft, random and alternating copolymers, terpolymers, and higher "x"mers, further including their analogs, derivatives, combinations, and blends thereof. Furthermore, unless otherwise specifically limited, the term "polymer" shall include all possible isomeric configurations of the molecule, including, but are not limited to isotactic, syndiotactic and random symmetries, and combinations thereof. Furthermore, unless otherwise specifically limited, the term "polymer" shall include all possible geometrical configurations of the molecule.

The methods and compositions of the present invention may comprise, consist essentially of, or consist of the components and ingredients of the present invention as well as other ingredients described herein. As used herein, "consisting essentially of" means that the methods, systems, apparatuses and compositions may include additional steps, components or ingredients, but only if the additional steps, components or ingredients do not materially alter the basic and novel characteristics of the claimed methods, systems, apparatuses, and compositions.

The term "actives" or "percent actives" or "percent by weight actives" or "actives concentration" are used interchangeably herein and refers to the concentration of those ingredients involved in cleaning expressed as a percentage minus inert ingredients such as water or salts. It is also sometimes indicated by a percentage in parentheses, for example, "chemical (10%)."

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

The term "surfactant" refers to a molecule having surface activity, including wetting agents, dispersants, emulsifiers, detergents, and foaming agents, and the like. It is understood to be inclusive of the use of a single surfactant or multiple surfactants.

The term "weight percent," "wt. %," "wt-%," "percent by weight," "% by weight," and variations thereof, as used herein, refer to the concentration of a substance as the weight of that substance divided by the total weight of the composition and multiplied by 100.

As used herein, the term "cleaning" refers to a method used to facilitate or aid in soil removal, bleaching, microbial population reduction, and any combination thereof. As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

The term "hard surface" refers to a solid, substantially non-flexible surface such as a counter top, tile, floor, wall, panel, window, plumbing fixture, kitchen and bathroom furniture, appliance, engine, circuit board, and dish. Hard surfaces may include for example, health care surfaces and food processing surfaces.

As used herein, the phrase "health care surface" refers to a surface of an instrument, a device, a cart, a cage, furniture, a structure, a building, or the like that is employed as part of a health care activity. Examples of health care surfaces include surfaces of medical or dental instruments, of medical or dental devices, of electronic apparatus employed for monitoring patient health, and of floors, walls, or fixtures of structures in which health care occurs. Health care surfaces are found in hospital, surgical, infirmity, birthing, mortuary, and clinical diagnosis rooms. These surfaces can be those typified as "hard surfaces" (such as walls, floors, bed-pans, etc.), or fabric surfaces, e.g., knit, woven, and non-woven surfaces (such as surgical garments, draperies, bed linens, bandages, etc.), or patient-care equipment (such as respirators, diagnostic equipment, shunts, body scopes, wheel chairs, beds, etc.), or surgical and diagnostic equipment. Health care surfaces include articles and surfaces employed in animal health care.

As used herein, the term "instrument" refers to the various medical or dental instruments or devices that can benefit from cleaning with a composition according to the present invention.

The term "laundry" refers to items or articles that are cleaned in a laundry washing machine. In general, laundry refers to any item or article made from or including textile materials, woven fabrics, non-woven fabrics, and knitted fabrics. The textile materials can include natural or synthetic fibers such as silk fibers, linen fibers, cotton fibers, polyester fibers, polyamide fibers such as nylon, acrylic fibers, acetate fibers, and blends thereof including cotton and polyester blends. The fibers can be treated or untreated. Exemplary treated fibers include those treated for flame retardancy. It should be understood that the term "linen" is often used to describe certain types of laundry items including bed sheets, pillow cases, towels, table linen, table cloth, bar mops and uniforms. The invention additionally provides a composition and method for treating non-laundry articles and surfaces including hard surfaces such as dishes, glasses, and other ware.

As used herein, the terms "emulsion" and "dispersion" refer to thermodynamically stable, isotropic dispersions of a component stabilized by an interfacial film of surfactant characterized by ultra-low interfacial tension. As described in greater detail herein the component contained within the emulsion can include a number of different types of materials, examples of which include, but are not limited to, fragrance, dyes, and oils.

As used herein, the phrases "medical instrument," "dental instrument," "medical device," "dental device," "medical equipment," or "dental equipment" refer to instruments, devices, tools, appliances, apparatus, and equipment used in medicine or dentistry. Such instruments, devices, and equipment can be cold sterilized, soaked or washed and then heat sterilized, or otherwise benefit from cleaning in a composition of the present invention. These various instruments, devices and equipment include, but are not limited to: diagnostic instruments, trays, pans, holders, racks, forceps, scissors, shears, saws (e.g. bone saws and their blades), hemostats, knives, chisels, rongeurs, files, nippers, drills, drill bits, rasps, burrs, spreaders, breakers, elevators, clamps, needle holders, carriers, clips, hooks, gouges, curettes, retractors, straightener, punches, extractors, scoops, keratomes, spatulas, expressors, trocars, dilators, cages, glassware, tubing, catheters, cannulas, plugs, stents, scopes (e.g., endoscopes, stethoscopes, and arthoscopes) and related equipment, and the like, or combinations thereof.

As used herein, the term "soil" or "stain" refers to a non-polar oily substance which may or may not contain particulate matter such as mineral clays, sand, natural mineral matter, carbon black, graphite, kaolin, environmental dust, etc.

As used herein, the term "substantially free" refers to compositions completely lacking the component or having such a small amount of the component that the component does not affect the performance of the composition. The component may be present as an impurity or as a contaminant and shall be less than 0.5 wt-%. In another embodiment, the amount of the component is less than 0.1 wt-% and in yet another embodiment, the amount of component is less than 0.01 wt-%.

The terms "vehicle" or "car" as used herein, refer to any transportation conveyance including without limitation, automobiles, trucks, sport utility vehicles, buses, trucks, motorcycles, monorails, diesel locomotives, passenger coaches, small single engine private airplanes, corporate jet aircraft, commercial airline equipment, etc.

As used herein, the term "ware" refers to items such as eating and cooking utensils, dishes, and other hard surfaces such as showers, sinks, toilets, bathtubs, countertops, windows, mirrors, transportation vehicles, and floors. As used herein, the term "warewashing" refers to washing, cleaning, or rinsing ware. Ware also refers to items made of plastic. Types of plastics that can be cleaned with the compositions according to the invention include but are not limited to, those that include polypropylene polymers (PP), polycarbonate polymers (PC), melamine formaldehyde resins or melamine resin (melamine), acrilonitrile-butadiene-styrene polymers (ABS), and polysulfone polymers (PS). Other exemplary plastics that can be cleaned using the compounds and compositions of the invention include polyethylene terephthalate (PET) polystyrene polyamide.

The terms "water soluble" and "water dispersible" as used herein, means that the polymer is soluble or dispersible in water in the inventive compositions. In general, the polymer should be soluble or dispersible at 25° C. at a concentration of 0.0001% by weight of the water solution and/or water carrier, preferably at 0.001%, more preferably at 0.01% and most preferably at 0.1%.

The methods, systems, apparatuses, and compositions of the present invention may comprise, consist essentially of, or consist of the components and ingredients of the present invention as well as other ingredients described herein. As used herein, "consisting essentially of" means that the methods, systems, apparatuses and compositions may include additional steps, components or ingredients, but only if the additional steps, components or ingredients do not materially alter the basic and novel characteristics of the claimed methods, systems, apparatuses, and compositions.

Compositions and Emulsions

Novel and improved emulsions are described herein. Those emulsions can be contained in liquid compositions and beneficially can be diluted to ultra-low levels while retaining their stability. These emulsions have many advantages over conventional emulsions. For example, the emulsions described herein are thermodynamically stable, isotropic dispersions of a component stabilized by an interfacial film of an emulsion surfactant characterized by ultra-low interfacial tension. The emulsions are dilutable such that the emulsion surfactant can be an at ultra-low concentration in a liquid composition while the emulsions retain their emulsified state even during and after dilution in the composition. Further, the emulsions leave little, or preferably no, residue on a surface after contact.

The emulsions comprise a surfactant, which forms the interfacial film of the emulsion. The emulsion can further comprise an additional surfactant which forms the interfacial film of the surfactant or contributes to its stability.

The emulsions can be contained within a composition. The compositions are preferably liquid. The liquid compositions thus can comprise a carrier and the emulsions described herein. Further, the emulsion and/or composition can comprise one or more additional ingredients. The additional ingredients can include, but are not limited to, an alkalizing agent, a chelating agent, a salt, an additional surfactant, or a combination thereof.

Encapsulated by the interfacial film of the emulsion can be one or more components. The emulsions and compositions described herein are not limited by the components that can be encapsulated within the emulsion. Components that can be encapsulated within the emulsion, include, but are not limited to, a dye, a fragrance, an oil, an encapsulated surfactant, water, or a combination thereof.

The emulsions beneficially are stable, i.e., retain their interfacial film, even upon dilution. The emulsions can be diluted within the composition at a ratio of emulsion to carrier of between about 1:2 to about 1:25, preferably about 1:5 to about 1:20, more preferably between about 1:10 and about 1:15. The carrier used to dilute the composition can be the same as the carrier the liquid composition is comprised of or it can be a different carrier whether miscible or immiscible in the composition's carrier.

Even upon dilution of the composition comprising the emulsions, the emulsions retain their stability. In a preferred embodiment, the stability can be retained at a temperature between about 10° C. and about 40° C., more preferably between about 15° C. and about 35° C., most preferably between about 20° C. and about 30° C.

Further, upon dilution of the composition comprising the emulsions, the emulsions retain their stability for at least a period of 1 hour, 2 hours, 3 hours, 6 hours, 12 hours, 18 hours, 24 hours, 36 hours, 48 hours, 60 hours, 72 hours, or more.

Carrier

As described herein the compositions comprise a first carrier. Further, the compositions can be diluted with a second carrier. The second carrier can be the same or different from the first carrier. In an embodiment where the second carrier is different from the first carrier, the second carrier can be miscible or immiscible with the first carrier.

Suitable carriers include, but are not limited to, water, a solvent, or a mixture thereof. The water can be soft (about 1 grain or less), slightly hard (between about 1 and about 3.5 grains), moderately hard (between about 3.5 grains and about 6 grains) or hard (about 6 grains or higher). Suitable solvents can include water miscible solvents, water immiscible solvents or a combination thereof.

Preferred solvents include, but are not limited to, glycol ethers, benzyl alcohol, or a combination thereof. Preferred glycol ether solvents include, but are not limited to, diethylene glycol n-butyl ether, diethylene glycol n-propyl ether, diethylene glycol ethyl ether, diethylene glycol methyl ether, diethylene glycol t-butyl ether, dipropylene glycol n-butyl ether, dipropylene glycol methyl ether, dipropylene glycol ethyl ether, dipropylene glycol propyl ether, dipropylene glycol tert-butyl ether, ethylene glycol butyl ether, ethylene glycol propyl ether, ethylene glycol ethyl ether, ethylene glycol methyl ether, ethylene glycol methyl ether acetate, propylene glycol n-butyl ether, propylene glycol ethyl ether, propylene glycol methyl ether, propylene glycol n-propyl ether, tripropylene glycol methyl ether and tripropylene glycol n-butyl ether, ethylene glycol phenyl ether, propylene glycol phenyl ether and mixtures thereof.

The carrier can comprise between about 80 wt. % and about 99 wt. % of the composition. In a preferred embodiment, the carrier can comprise at least about 81, 82, 83, 84, 85, 86, 87, 88, 89, 90, 91, 92, 93, 94, 95, 96, 97, 98, or 99 wt. % of the composition. In a preferred embodiment, the carrier comprises between about 85 wt. % and about 95 wt. %. In another preferred embodiment, the carrier comprises between about 90 wt. % and about 99 wt. %.

Surfactant

As described herein the emulsions comprise a surfactant. Suitable surfactants can comprise, consist essentially of, or consist of a copolymer comprising acrylic acid, an alcohol alkoxylate, a tertiary amine, a quaternary amine, or a mixture thereof. Preferred surfactants have an HLB of at least about 6, more preferably at least about 7, or most preferably at least about 8. In a preferred embodiment, the HLB is between about 6 and about 15, more preferably between about 7 and about 14, and most preferably between about 8 and about 12.

The surfactant can comprise between about 0.01 wt. % and about 1 wt. % of the composition. In a preferred embodiment, the composition can comprise between about 0.01 wt. % and about 0.5 wt. % of surfactant, more preferably between about 0.01 wt. % and about 0.1 wt. %. In a preferred embodiment, the composition can comprise between about 0.1 wt. % and about 1 wt. % of surfactant, more preferably between about 0.3 wt. % and about 1 wt. %.

The emulsion forming surfactant preferably comprises a copolymer comprising acrylic acid. In a preferred embodiment, the copolymer comprising acrylic acid is crosslinked.

Preferably, the copolymer is a crosslinked copolymer of acrylic acid and an alkyl acrylate. Preferred alkyl acrylates can have an alkyl group of between C1 and C40, more preferably between about C5 and C35, most preferably between C10 and C30. A preferred alkyl acrylate is methacrylate. In a most preferred embodiment, the surfactant comprises a crosslinked copolymer of acrylic acid and methacrylate.

The emulsion and/or composition can further comprise one or more additional surfactants to improve the interfacial film and/or viscosity of the compositions comprising the emulsions. Preferred surfactants include, an alcohol alkoxylate, a tertiary amine, a quaternary amine or mixture thereof.

Preferred alcohol alkoxylates include ethylene oxide, propylene oxide, and butylene oxide groups and mixtures thereof. Particularly, suitable alcohol alkoxylates can have between about 1 and about 30 moles of alkyl oxide and carbon chains between about 4 and about 20 carbons in length. In a preferred embodiment the alcohol ethoxylate may be a C8-C18 alcohol alkoxylate with about 10 to about 40 moles of alkyl oxide. In a more preferred embodiment the alcohol alkoxylate may be a C8-C16 alcohol alkoxylate with about 10 to about 30 moles of alkyl oxide. In an even more preferred embodiment, the alcohol alkoxylate may be a C10-C12 alcohol alkoxylate with about 15 to about 25 moles of alkyl oxide. Examples of preferred alcohol alkoxylates are available under the brands Neodol (available from Shell) and Tomadol (available from Evonik).

Preferred tertiary amines include amine oxides corresponding to the general formula:

wherein the arrow is a conventional representation of a semi-polar bond; and, $R^1$, $R^2$, and $R^3$ may be aliphatic, aromatic, heterocyclic, alicyclic, or combinations thereof. Generally, for amine oxides of detergent interest, $R^1$ is an alkyl radical of from about 8 to about 24 carbon atoms; $R^2$ and $R^3$ are alkyl or hydroxyalkyl of 1-3 carbon atoms or a mixture thereof; $R^2$ and $R^3$ can be attached to each other, e.g. through an oxygen or nitrogen atom, to form a ring structure; $R^4$ is an alkylene or a hydroxyalkylene group containing 2 to 3 carbon atoms; and n ranges from 0 to about 20. An amine oxide can be generated from the corresponding amine and an oxidizing agent, such as hydrogen peroxide.

Suitable amine oxides, can include, but are not limited to octyl, decyl, dodecyl, isododecyl, coconut, or tallow alkyl di-(lower alkyl) amine oxides, specific examples of which are octyldimethylamine oxide, nonyldimethylamine oxide, decyldimethylamine oxide, undecyldimethylamine oxide, dodecyldimethylamine oxide, iso-dodecyldimethyl amine oxide, tridecyldimethylamine oxide, tetradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl)amine oxide, 3,6,9-trioctadecyldimethylamine oxide and 3-dodecoxy-2-hydroxypropyldi-(2-hydroxyethyl)amine oxide. Preferred tertiary amines and quaternary amines include, but are not limited to, those sold under the tradename TOMAMINE by Evonik.

Additional Ingredients

The composition and/or emulsion can optionally comprise an alkalizing agent, a chelating agent, a salt, a thickener, or a mixture thereof. Other optional ingredients can also be included in the compositions provided they do not negatively affect the emulsions.

Alkalizing Agent

The compositions and emulsions can optionally include an alkalizing agent to adjust the pH. Preferably, the pH is between about 6 and about 8, more preferably between about 6.5 and about 7.8, most preferably between about 6.8 and about 7.5. The pH can be adjusted to a desired pH by the addition of an alkalizing agent. Suitable alkalizing agents include, but are not limited to alkali metal carbonates, alkali metal hydroxides, metal borates, silicates, and organic bases.

Exemplary alkali metal carbonates include, but are not limited to, sodium carbonate, potassium carbonate, bicarbonate, sesquicarbonate, and mixtures thereof. Exemplary alkali metal hydroxides include, but are not limited to sodium, lithium, or potassium hydroxide. Exemplary metal silicates include, but are not limited to, sodium or potassium silicate or metasilicate. Exemplary metal borates include, but are not limited to, sodium or potassium borate. Organic alkalizing agents are often strong nitrogen bases including, for example, ammonia (ammonium hydroxide), amines, alkanolamines, and amino alcohols. Typical examples of amines include primary, secondary or tertiary amines and diamines carrying at least one nitrogen linked hydrocarbon group, which represents a saturated or unsaturated linear or branched alkyl group having at least 10 carbon atoms and preferably 16-24 carbon atoms, or an aryl, aralkyl, or alkaryl group containing up to 24 carbon atoms, and wherein the optional other nitrogen linked groups are formed by optionally substituted alkyl groups, aryl group or aralkyl groups or polyalkoxy groups. Typical examples of alkanolamines include monoethanolamine, monopropanolamine, diethanolamine, dipropanolamine, triethanolamine, tripropanolamine and the like. Typical examples of amino alcohols include 2-amino-2-methyl-1-propanol, 2-amino-1-butanol, 2-amino-2-methyl-1,3-propanediol, 2-amino-2-ethyl-1,3-propanediol, hydroxymethyl aminomethane, and the like.

When the compositions and/or emulsions comprise an alkalizing agent it can be added in any suitable amount to arrive at the desired pH. In a preferred embodiment, the alkalizing agent is in a concentration between about 0.01 wt. % and about 10 wt. %; more preferably between about 0.01 wt. % and about 5 wt. %, most preferably between about 0.01 wt. % and about 1 wt. %.

Chelating Agent

The compositions and emulsions can optionally include a chelating agent (or sequestering agent). While chelation and sequestering are different chemical mechanisms, for convenience the two are referred to as chelating agents herein. If the compositions comprise or are diluted with hard water, it can be preferred to include a chelating agent. In general, a chelating agent is a molecule capable of coordinating (i.e., binding) the metal ions commonly found in water sources to prevent the metal ions from interfering with the action of the other ingredients of the composition and/or emulsion. In a preferred embodiment, the compositions and/or emulsions are phosphate-free and/or sulfate-free. In embodiments of the solid cleaning composition that are phosphate-free, the additional functional materials, including chelating agents exclude phosphorous-containing compounds such as condensed phosphates and phosphonates.

Suitable chelating agents include aminocarboxylates and polycarboxylates. Some examples of aminocarboxylates useful as chelating, include, N-hydroxyethyliminodiacetic acid, nitrilotriacetic acid (NTA), ethylenediaminetetraacetic acid (EDTA), N-hydroxyethyl-ethylenediaminetriacetic acid (HEDTA), diethylenetriaminepentaacetic acid (DTPA), and the like. Some examples of polymeric polycarboxylates suitable for use as sequestering agents include those having a pendant carboxylate (—$CO_2$) groups and include, for example, polyacrylic acid, maleic/olefin copolymer, acrylic/maleic copolymer, polymethacrylic acid, acrylic acid-methacrylic acid copolymers, hydrolyzed polyacrylamide, hydrolyzed polymethacrylamide, hydrolyzed polyamidemethacrylamide copolymers, hydrolyzed polyacrylonitrile, hydrolyzed polymethacrylonitrile, hydrolyzed acrylonitrile-methacrylonitrile copolymers, and the like.

In embodiments where the compositions and/or emulsions are not phosphate-free, chelating agents may include, for example a condensed phosphate, a phosphonate, and the like. Some examples of condensed phosphates include sodium and potassium orthophosphate, sodium and potassium pyrophosphate, sodium tripolyphosphate, sodium hexametaphosphate, and the like.

In embodiments where the compositions and/or emulsions are not phosphate-free, the composition may include a phosphonate such as 1-hydroxyethane-1,1-diphosphonic acid $CH_3C(OH)[PO(OH)_2]_2$; aminotri(methylenephosphonic acid) $N[CH_2 PO(OH)_2]_3$; aminotri(methylenephosphonate), sodium salt 2-hydroxyethyliminobis(methylenephosphonic acid) $HOCH_2 CH_2 N[CH_2 PO(OH)_2]_2$; diethylenetriaminepenta (methylenephosphonic acid) $(HO)_2 POCH_2 N[CH_2 N[CH_2 PO(OH)_2]_2]_2$; diethylenetriaminepenta(methylenephosphonate), sodium salt $C_9 H_{(28-x)} N_3 Na_x O_{15} P_5$ (x=7); hexamethylenediamine(tetramethylenephosphonate), potassium salt $C_{10} H_{(28-x)} N_2 K_x O_{12} P_4$ (x=6); bis(hexamethylene)triamine (pentamethylenephosphonic acid) $(HO_2)POCH_2N[(CH_2)_6 N[CH_2 PO(OH)_2]_2]_2$; and phosphorus acid $H_3PO_3$. In some embodiments, a phosphonate combination such as ATMP and DTPMP may be used. A neutralized or alkaline phosphonate, or a combination of the phosphonate with an alkali source prior to being added into the mixture such that there is little or no heat or gas generated by a neutralization reaction when the phosphonate is added can be used.

For a further discussion of chelating agents, see Kirk-Othmer, Encyclopedia of Chemical Technology, Third Edition, volume 5, pages 339-366 and volume 23, pages 319-320, the disclosure of which is incorporated by reference herein.

When the compositions and/or emulsions comprise a chelating agent it can be added in any suitable amount to reduce the water hardness. In a preferred embodiment, the chelating agent is in a concentration between about 0.01 wt. % and about 5 wt. %; more preferably between about 0.01 wt. % and about 1.5 wt. %, most preferably between about 0.01 wt. % and about 1 wt. %.

Salt

The compositions and emulsions can optionally include a salt. It has been found that in some embodiments, the salt can improve the flowability of the compositions comprising an emulsion. Preferred salts include halide salts. More preferably the salt is a chloride salt. Most preferably the salt is an alkali metal chloride.

When the compositions and/or emulsions comprise a chelating agent it can be added in any suitable amount to reduce the water hardness. In a preferred embodiment, the chelating agent is in a concentration between about 0.01 wt. % and about 1 wt. %; more preferably between about 0.01 wt. % and about 0.5 wt. %.

Thickener

The compositions and emulsions can optionally include a thickener. Suitable thickeners can include those which do not leave contaminating residue on the surface to be treated. Generally, thickeners which may be used in the present invention include natural gums such as xanthan gum, guar gum, modified guar, or other gums from plant mucilage; polysaccharide-based thickeners (such as carrageenan), such as alginates, starches, and cellulosic polymers (e.g., carboxymethyl cellulose, hydroxyethyl cellulose, and the like); polyacrylates thickeners; and hydrocolloid thickeners, such as pectin.

Generally, the concentration of thickener employed in the present compositions or methods will be dictated by the desired viscosity within the final composition. In a preferred embodiment, the thickener is in a concentration between about 0.01 wt. % and about 5 wt. %; more preferably between about 0.01 wt. % and about 1.5 wt. %, most preferably between about 0.01 wt. % and about 1 wt. %.

Encapsulated Ingredients

A variety of ingredients can be encapsulated within the emulsion. Such ingredients, can include, but are not limited to, a dye, a fragrance, an oil, or a mixture thereof. Many other components can be encapsulated within the emulsion provided they do not negatively affect the emulsions; thus, the emulsions are not limited by what can be encapsulated. Depending on the carrier and emulsion a dye and/or fragrance may be encapsulated within the emulsion or present in the composition.

When the emulsions comprise an encapsulated component, the encapsulated components are preferably in a concentration between about 0.1 wt. % and about 15 wt. %; more preferably between about 1 wt. % and about 12 wt. %; most preferably between about 5 wt. % and about 10 wt. %.

Dyes and Fragrances

Various dyes, odorants including perfumes, and other aesthetic enhancing agents may also be included in the detergent composition. Dyes may be included to alter the appearance of the composition, as for example, any of a variety of FD&C dyes, D&C dyes, and the like. Additional suitable dyes include Direct Blue 86 (Miles), Fastusol Blue (Mobay Chemical Corp.), Acid Orange 7 (American Cyanamid), Basic Violet 10 (Sandoz), Acid Yellow 23 (GAF), Acid Yellow 17 (Sigma Chemical), Sap Green (Keystone Aniline and Chemical), Metanil Yellow (Keystone Aniline and Chemical), Acid Blue 9 (Hilton Davis), Sandolan Blue/Acid Blue 182 (Sandoz), Hisol Fast Red (Capitol Color and Chemical), Fluorescein (Capitol Color and Chemical), Acid Green 25 (Ciba-Geigy), Pylakor Acid Bright Red (Pylam), and the like. Fragrances or perfumes that may be included in the compositions include, for example, terpenoids such as citronellol, aldehydes such as amyl cinnamaldehyde, a jasmine such as C1S-jasmine or jasmal, vanillin, and the like.

When the emulsions comprise an encapsulated dye and/or fragrance, the encapsulated dye and/or fragrance is preferably in a concentration between about 0.1 wt. % and about 15 wt. %; more preferably between about 1 wt. % and about 12 wt. %; most preferably between about 1 wt. % and about 10 wt. %.

Encapsulated Surfactant

In some embodiments, one or more surfactants can be encapsulated within the emulsion. Such surfactants are not limited except that they cannot negatively affect the emulsion. Suitable encapsulated surfactants can comprise an amphoteric surfactant, anionic surfactant, cationic surfactant, nonionic surfactant, zwitterionic surfactant, or mixture thereof.

When the emulsions comprise an encapsulated surfactant, the encapsulated surfactant is preferably in a concentration between about 0.1 wt. % and about 15 wt. %; more preferably between about 1 wt. % and about 12 wt. %; most preferably between about 1 wt. % and about 10 wt. %.

Hydrophobic Components

In some embodiments, one or more hydrophobic components can be encapsulated within the emulsion. Preferred hydrophobic components include but are not limited to oils, lubricants, mineral oil, moisturizers, and the like.

When the emulsions comprise a hydrophobic component, the hydrophobic component is preferably in a concentration between about 0.1 wt. % and about 15 wt. %; more preferably between about 1 wt. % and about 12 wt. %; most preferably between about 1 wt. % and about 10 wt. %.

For exemplary purposes, Table 1 provides nonlimiting examples of concentration ranges of the composition and emulsion ingredients and encapsulated ingredients.

TABLE 1

| Composition and Emulsion Ingredients | Exemplary Formulation Concentrations (wt. %) | | |
|---|---|---|---|
| Carrier | 80-99 | 85-99 | 90-99 |
| Surfactant | 0.01-1 | 0.01-1 | 0.01-1 |
| Alkalizing Agent | 0-10 | 0.01-5 | 0.01-1 |
| Chelating Agent | 0-5 | 0.01-1.5 | 0.1-1 |
| Salt | 0-1 | 0.01-1 | 0.01-0.5 |
| Thickener | 0-1 | 0.01-1.5 | 0.1-1 |
| Encapsulated Ingredients | 0.1-15 | 1-12 | 5-10 |
| Dye | 0-15 | 0.1-12 | 1-10 |
| Encapsulated Surfactant | 0-15 | 0.1-12 | 1-10 |
| Fragrance | 0-15 | 0.1-12 | 1-10 |
| Hydrophobic Component | 0-15 | 0.1-12 | 1-10 |

Methods of Manufacture

The compositions can be prepared by first preparing an emulsion by mixing a surfactant with an ingredient to be encapsulated and adding the mixture to a first carrier to form a composition comprising an emulsion. Other composition and emulsion ingredients (e.g., alkalizing agent, chelating agent, salt, and/or thickener) can be added during this process as well. The composition can then be diluted with a second carrier to a desired volume, concentration, and/or viscosity.

Methods of Using the Compositions

The compositions comprising an emulsion can be contacted with a surface as defined herein. Optionally, after contact, the surface can be rinsed. A benefit of the compositions is that they leave little visible residue, preferably no visible residue on the surface.

EXAMPLES

Embodiments of the present invention are further defined in the following non-limiting examples. It should be understood that these examples, while indicating certain embodiments of the invention, are given by way of illustration only. The particular materials and amounts, as well as other conditions and details, recited therein should not be construed to unduly limit this invention. From the above discussion and these examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

The materials used in the following examples are provided herein:

Laponite RD: A synthetic, layered silicate.

Carbopol 2020: A cross-linked copolymer of acrylic acid C10-C30 alkyl acrylate available from Lubrizol.

Carbopol 940: A copolymer of acrylic acid C10-C30 alkyl acrylate available from Lubrizol.

Carbopol 941: A copolymer of acrylic acid C10-C30 alkyl acrylate available from Lubrizol.

Pemulen 1621: A moderately cross-linked copolymer of acrylic acid C10-C30 alkyl acrylate available from Lubrizol.

Pemulen 1622: A lightly cross-linked copolymer of acrylic acid C10-C30 alkyl acrylate available from Lubrizol.

Dowanol DPnP: 1-(2-propoxy-2-methylethoxy) 2-propanol, a slow-evaporating glycol ether available from Dow Chemical.

Neodol 25-12: C12-C15 alcohol ethoxylate with 7 moles of ethylene oxide, available from Shell.

Neodol 91-6: C9-C11 alcohol ethoxylate with 6 moles of ethylene oxide per mole of alcohol, available from Shell.

Tomadol 25-7: C12-C15 ethoxylated alcohol, available from Evonik.

Tomamine E-14-2: An ethoxylated amine surfactant available from Evonik.

Tomamine Q-14-2: 75% active ether amine quaternary ammonia surfactant in isopropyl alcohol, available from Evonik.

Tomamine Q-C-15: A quaternary amine grade of 100% coco poly (15) oxyethylene methyl ammonium chloride, available from Evonik.

Tomamine AO-405: An alkyloxypropylamine oxide available from Evonik.

Tomamine AO-455: An alkyloxypropylamine oxide available from Evonik.

Tomadol 901: an exemplary ethoxylated alcohol having a carbon chain length of C9-C11, available from Evonik.

Tomadol 902: an exemplary ethoxylated alcohol having a carbon chain length of C9-C11, available from Evonik.

Hamposyl L: Lauroyl sarcosine available from Chatten Chemicals, Inc.

Hamposyl M: Myristoyl sarcosine available from Chattem Chemicals, Inc.

Hamposyl C: Cocoyl sarcosine available from Chattem Chemicals, Inc.

Glucopon 625: D-Glucopyranose, oligomeric, C10-16-alkyl glycoside, available from BASF.

Amphosol CA: Cocamidopropyl betaine, available from Stepan Company.

Aromox C/12 W: Cocobis(2-hydroxyethyl) amine oxide, available from Akzo Nobel Surface Chemistry.

Berol R648: Alkyl polyglycol ether ammonium methyl chloride, available from Akzo Nobel Surface Chemistry.

Calfax 6LA-70: C6 (linear) diphenyl oxide disulfonic acid, available from Pilot Chemical Co.

SilSurf J-1015-O: A silicone polyether available from Siltech Corporation.

Trilon M: An aqueous solution of trisodium nitrilotriacetate available by BASF.

NaCl: A solution of 20% sodium chloride.

NaOH: A solution of 50% sodium hydroxide.

Various commercially available common lab equipment and chemicals including: xanthan gum, citric acid, mineral oil, electric plate with magnetic stir bar, oven, stand mixer, sodium lauryl sulfate (SLS) Powder, sodium stearate, sodium polyacrylate, sodium acrylate, sodium laureth sulfate (SLES), carrageenan, and an exemplary fragrance.

Example 1

Laponite, xanthan gum, and mineral oil were combined with electric plate and magnetic stir bar at 350 rpm for approximately five minutes. Water was then to a total of 100 grams of solution and mixed for 15 minutes at 1000 rpm. The solution was visually inspected, initially, for separation, and again after a longer time interval. One sample was left at room temperature and another in a 50° C. oven. Due to the high viscosity of the solutions, as well as needing several times more polymer than the other candidates, xanthan gum was not tested further.

TABLE 2

Laponite With Xanthan Gum.

| % Laponite | % Xanthan | % Mineral Oil | Water | Interval | Results |
| --- | --- | --- | --- | --- | --- |
| 0.8 | 0.15 | 1 | DI | 24 hours | Unstable |
| 0.8 | 0.1 | 1 | DI | 24 hours | Unstable |
| 0.8 | 0.05 | 1 | DI | Immediately unstable | |
| 0.8 | 0.03 | 1 | DI | Immediately unstable | |
| 0.6 | 0.5 | 1 | DI | 24 hours | Stable |
| 0.8 | 0.2 | 1 | DI | Over night | Unstable |
| 0.6 | 0.2 | 1 | DI | Over night | Unstable |
| 0.4 | 0.2 | 1 | DI | Over night | Unstable |
| 0.2 | 0.2 | 1 | DI | Over night | Unstable |
| 0.1 | 0.2 | 1 | DI | Over night | Unstable |
| 0.6 | 0.4 | 1 | 5 grain | 24 hours | Unstable |
| 0.6 | 0.3 | 1 | 5 grain | 24 hours | Unstable |
| 0.54 | 0.5 | 1 | DI | 24 hours | Unstable |
| 0.6 | 0.5 | 1 | DI | 24 hours | Unstable |
| 0.66 | 0.5 | 1 | DI | 24 hours | Stable |
| 0.6 | 0.45 | 1 | DI | 24 hours | Unstable |
| 0.6 | 0.55 | 1 | DI | 24 hours | Stable |

A mixture of Laponite, Carbopol 2020, and mineral oil were mixed using an electric plate with a magnetic stir bar at 350 rpm for approximately five minutes. Water was added to comprise a 100 gram solution, and mixing continued at 350 rpm until visibly smooth, increasing the speed to 500 rpm if viscosity of the solution allowed. An initial visual inspection was made looking for separation of the oil from the solution. A final assessment was made after an interval of either overnight or seven days: one sample at room temperature and another in a 50° C. oven.

TABLE 3

Laponite With Carbopol 2020 Polmer.

| % Laponite | % Carbopol 2020 | % Mineral Oil | Water | Interval | Results |
| --- | --- | --- | --- | --- | --- |
| 0.8 | 0.2 | 1 | DI | Over night | Stable |
| 0.6 | 0.2 | 1 | DI | Over night | Stable |
| 0.4 | 0.2 | 1 | DI | Over night | Stable |
| 0.2 | 0.2 | 1 | DI | Over night | Stable |
| 0.1 | 0.2 | 1 | 5 grain | Over night | Unstable |
| 0.8 | 0.15 | 1 | DI | Over night | Stable |
| 0.8 | 0.1 | 1 | DI | Over night | Unstable |
| 0.8 | 0.05 | 1 | DI | Over night | Unstable |
| 0.8 | 0.001 | 1 | DI | Over night | Unstable |
| 0.2 | 0.15 | 1 | DI | 7 days | Stable |
| 0.22 | 0.15 | 1 | DI | 7 days | Stable |
| 0.18 | 0.15 | 1 | DI | 7 days | Stable |
| 0.2 | 0.165 | 1 | DI | 7 days | Stable |
| 0.2 | 0.135 | 1 | DI | 7 days | Stable |

A mixture of Laponite, Carbopol 940, and deionized water were mixed using an electric plate with a magnetic stir bar at 500 rpm, then increased to 1000 rpm after adding mineral oil. Citric acid was added as needed to reach a pH of seven. An initial visual inspection was made looking for separation of the oil from the solution. A final assessment was made after an interval of 18 or 24 hours, both at room temperature and 50° C.

TABLE 4

Laponite With Carbopol 940 Polymer.

| % Laponite | % Carbopol 940 | % Mineral Oil | % Citric Acid | Water | Interval | Results |
| --- | --- | --- | --- | --- | --- | --- |
| 0.8 | 0.2 | 1 | 0 | DI | 18 hours | Stable |
| 0.6 | 0.2 | 1 | 0 | DI | 18 hours | Stable |
| 0.4 | 0.2 | 1 | 0 | DI | 18 hours | Stable |
| 0.2 | 0.2 | 1 | 0 | DI | 18 hours | Stable |
| 0.1 | 0.2 | 1 | 0 | DI | 18 hours | Stable |
| 0.1 | 0.15 | 1 | 0 | DI | 24 hours | Unstable |
| 0.1 | 0.1 | 1 | 0 | DI | Immediately unstable | |
| 0.1 | 0.05 | 1 | 0 | DI | Immediately unstable | |
| 0.1 | 0.01 | 1 | 0.03 | DI | Immediately unstable | |
| 0.8 | 0.05 | 1 | 0 | DI | Immediately unstable | |
| 0.8 | 0.01 | 1 | 0.03 | DI | Immediately unstable | |
| 0.1 | 0.3 | 1 | 0 | DI | 24 hours | Stable |
| 0.2 | 0.2 | 1 | 0 | DI | 24 hours | Stable |
| 0.4 | 0.1 | 1 | 0 | DI | 24 hours | Stable |

A mixture of Laponite, Carbopol 941, and mineral oil were mixed using an electric plate with a magnetic stir bar at 350 rpm for approximately five minutes. Deionized water was added to until the solution weighed 100 grams. Mixing was continued at 350 rpm until visibly smooth, increasing the speed to 500 rpm if viscosity of the solution allowed. An initial visual inspection was made looking for separation of the oil from the solution. The samples were left overnight, for 48 hours, or for 4 days and reviewed the following day to evaluate whether the emulsion was stable. One sample at room temperature and another in a 50° C. oven.

TABLE 5

Laponite With Carbopol 941 Polymer.

| % Laponite | % Carbopol 941 | % Mineral Oil | Water | Interval | Results |
|---|---|---|---|---|---|
| 0.8 | 0.2 | 1 | DI | Over night | Stable |
| 0.6 | 0.2 | 1 | DI | Over night | Stable |
| 0.4 | 0.2 | 1 | DI | Over night | Stable |
| 0.2 | 0.2 | 1 | DI | Over night | Stable |
| 0.1 | 0.2 | 1 | DI | Over night | Stable |
| 0.4 | 0.15 | 1 | DI | Over night | Stable |
| 0.4 | 0.1 | 1 | DI | 48 hours | Stable |
| 0.4 | 0.05 | 1 | DI | Over night | Unstable |
| 0.4 | 0.01 | 1 | DI | Over night | Unstable |
| 0.3 | 0.1 | 1 | DI | 4 days | Stable |
| 0.3 | 0.11 | 1 | DI | 4 days | Stable |
| 0.3 | 0.09 | 1 | DI | 4 days | Stable |
| 0.33 | 0.1 | 1 | DI | 4 days | Stable |
| 0.27 | 0.1 | 1 | DI | 4 days | Stable |

A mixture of Laponite and five-grain water was created to which a premix of Pemulen 1621 and mineral oil was combined. Sodium hydroxide was added to achieve a pH of seven. The solution was mixed for 15 minutes at 1000 rpm. An initial visual inspection was made looking for separation of the oil from the solution. A final assessment was made after an interval of 24 hours: one sample at room temperature and another in a 50° C. oven

TABLE 6

Laponite With Pemulen 1621 Polymer.

| % Laponite | % Pemulen 1621 | % Mineral Oil | % NaOH | Water | Interval | Results |
|---|---|---|---|---|---|---|
| 0.8 | 0.1 | 1 | 0.06 | 5 grain | 24 hours | Stable |
| 0.6 | 0.1 | 1 | 0.06 | 5 grain | 24 hours | Stable |
| 0.4 | 0.1 | 1 | 0.06 | 5 grain | 24 hours | Stable |
| 0.2 | 0.1 | 1 | 0.06 | 5 grain | 24 hours | Stable |
| 0.1 | 0.1 | 1 | 0.06 | 5 grain | 24 hours | Stable |
| 0.8 | 0.2 | 1 | 0.06 | 5 grain | 24 hours | Stable |
| 0.8 | 0.1 | 1 | 0.06 | 5 grain | 24 hours | Stable |
| 0.8 | 0.05 | 1 | 0.06 | 5 grain | Immediately | unstable |
| 0.8 | 0.01 | 1 | 0.06 | 5 grain | Immediately | unstable |
| 0.11 | 0.1 | 1 | 0.06 | 5 grain | 24 hours | Stable |
| 0.09 | 0.1 | 1 | 0.06 | 5 grain | 24 hours | Stable |
| 0.1 | 0.11 | 1 | 0.06 | 5 grain | 24 hours | Stable |
| 0.1 | 0.09 | 1 | 0.06 | 5 grain | 24 hours | Stable |

A mixture of Laponite, Pemulen 1622, and mineral oil were mixed using an electric plate with a magnetic stir bar at 350 rpm for approximately five minutes. Deionized water was added to comprise a 100-gram solution, and sodium hydroxide was added to achieve a pH of seven. Mixing continued at 350 rpm until visibly smooth, increasing the speed to 500 rpm if viscosity of the solution allowed. An initial visual inspection was made looking for separation of the oil from the solution. A final assessment was made after an interval of either two or four days: one sample at room temperature and another in a 50° C. oven.

TABLE 7

Laponite With Pemulen 1622 Polymer Results.

| % Laponite | % Pemulen 1622 | % Mineral Oil | % NaOH | Water | Interval | Results |
|---|---|---|---|---|---|---|
| 0.8 | 0.1 | 1 | 0.06 | DI | 2 days | Stable |
| 0.6 | 0.1 | 1 | 0.06 | DI | 2 days | Stable |
| 0.4 | 0.1 | 1 | 0.06 | DI | 2 days | Stable |
| 0.2 | 0.1 | 1 | 0.06 | DI | 2 days | Stable |
| 0.1 | 0.1 | 1 | 0.06 | DI | 2 days | Stable |
| 0.8 | 0.2 | 1 | 0.06 | DI | 2 days | Stable |
| 0.8 | 0.1 | 1 | 0.06 | DI | 2 days | Stable |
| 0.8 | 0.05 | 1 | 0.06 | DI | 2 days | Unstable |
| 0.8 | 0.01 | 1 | 0.06 | DI | Immediately | unstable |
| 0.1 | 0.1 | 1 | 0.06 | DI | 4 days | Stable |
| 0.1 | 0.11 | 1 | 0.06 | DI | 4 days | Stable |
| 0.1 | 0.09 | 1 | 0.06 | DI | 4 days | Stable |
| 0.11 | 0.1 | 1 | 0.06 | DI | 4 days | Stable |
| 0.09 | 0.1 | 1 | 0.06 | DI | 4 days | Stable |

Certain polymers discussed above were selected for further testing because of the relatively small amount of polymer required to disperse 1.0 g of mineral oil.

Polymer was gently swirled together with 10 grams of mineral oil, while separately Laponite and water were mixed with a magnetic stir bar. Once the Laponite was well-dispersed, the two solutions were combined using a stand mixer with a medium shear blade at 1000 rpm for 15 minutes. The solvent DPnP was added to test the emulsion in solvent dilution. Sodium hydroxide was added if needed to adjust pH to seven. 10 grams of the concentrate and 90 grams of five-grain water were combined at 300 rpm using a magnetic stir bar until the concentrate was completely dispersed. The solution was then visually inspected for separation after being left at room temperature overnight, and again after about one week. The Pemulen polymers showed the best ability to hold particles in suspension with the lowest relative viscosity, and was thus selected to continue testing with various surfactants.

TABLE 8

Polymer Concentrate Test Results.

| Laponite | Carbopol 2020 | Carbopol 940 | Carbopol 941 | Pemulen 1621 | Pemulen 1622 | DPnP | NaOH | Results |
|---|---|---|---|---|---|---|---|---|
| 2 g | 1.35 g | 0 | 0 | 0 | 0 | log | 0 | Good |
| 4 g | 0 | 1 g | 0 | 0 | 0 | log | 0 | Poor |
| 3 g | 0 | 0 | 0.9 g | 0 | 0 | log | 0 | Poor |
| 1 g | 0 | 0 | 0 | 0.9 g | 0 | log | 0.46 g | Best |
| 1 g | 0 | 0 | 0 | 0.9 g | 0 | 20 g | 0 | Best |
| 1 g | 0 | 0 | 0 | 0 | 0.9 g | 10 g | 0.40 g | Best |

The emulsions were visually inspected and rated as poor, good, or best. Poor indicated that the emulsion did not remain stable upon dilution. Good indicated that the emulsion was dilutable and remained generally stable. Best indicated an emulsion that remained stable following dilution. It was found that the Pemulen dispersions provided the best stability. Carbopol 2020 also provided good stability. The Pemulen and Carbopol 2020 surfactants are cross-linked copolymers of acrylic acid C10-C30 alkyl acrylates.

Example 2

Figure 1A:
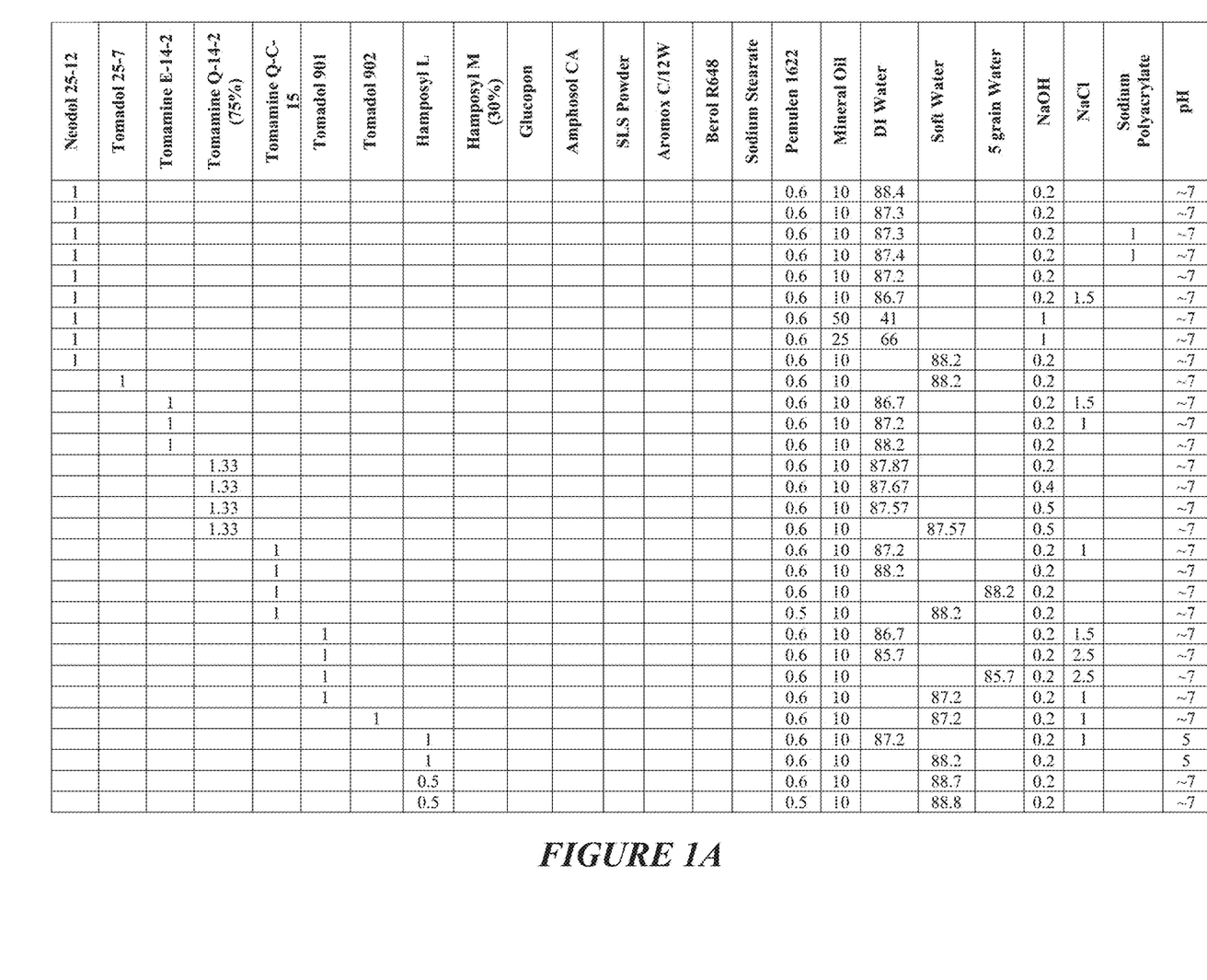
Figure 1B:
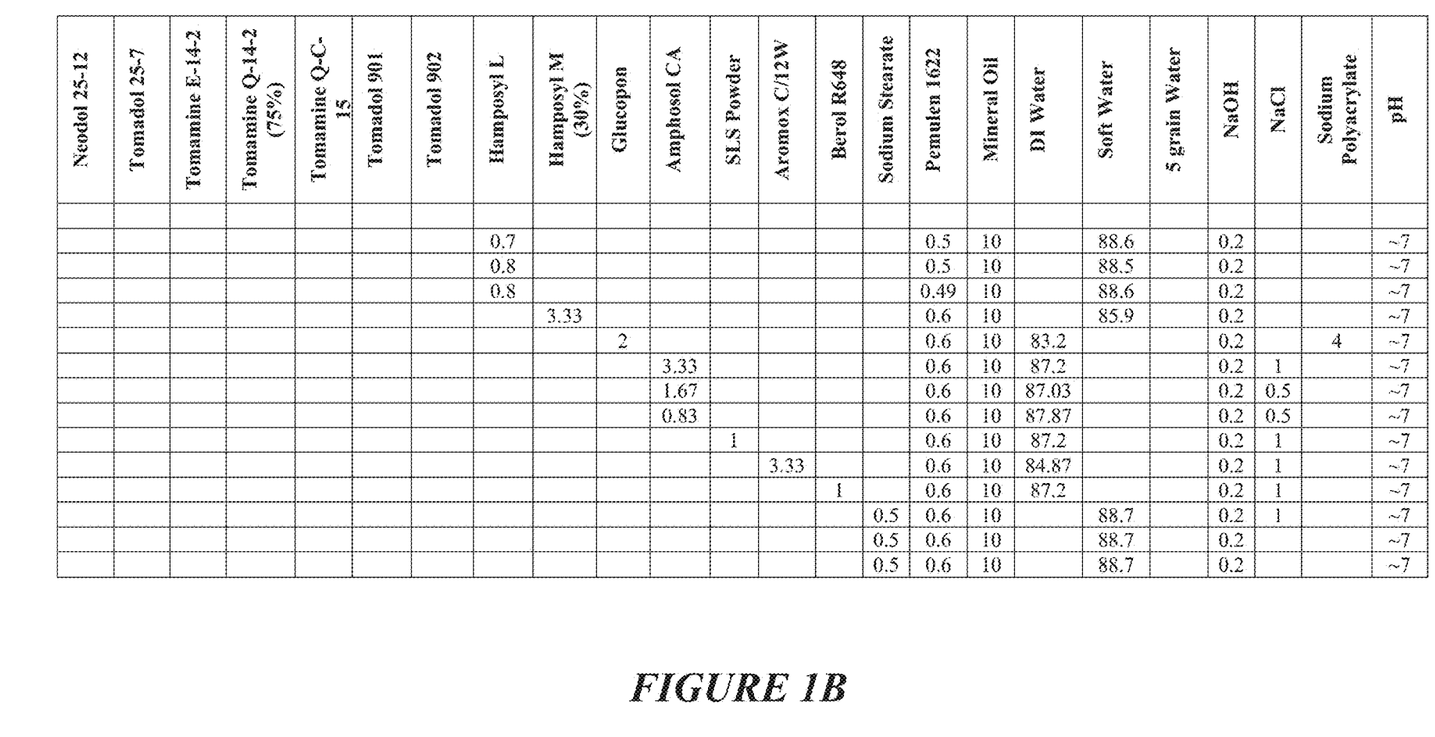

Pemulen 1622 was dispersed in mineral oil using a stand mixer with a medium shear blade running at 300 rpm for three minutes. The water was added and mixing continued at 1000 rpm for five minutes. The specified amount of sodium hydroxide was added and mixed for another 10 minutes. Then the surfactant was added, taking note of viscosity and droplet size. Salt may have been added for viscosity control. The concentration was then diluted 10 times with five-grain water and visually assessed. The surfactants that yield the lowest viscosity while producing the best dilution (i.e., retained a stable dispersion upon dilution) are Hamposyl L, Hamposyl M, Tomadol 901, Tomadol 902, Neodol 25-12, and sodium stearate. The testing details are outlined in FIGS. 1A and 1B.

Figure 2:
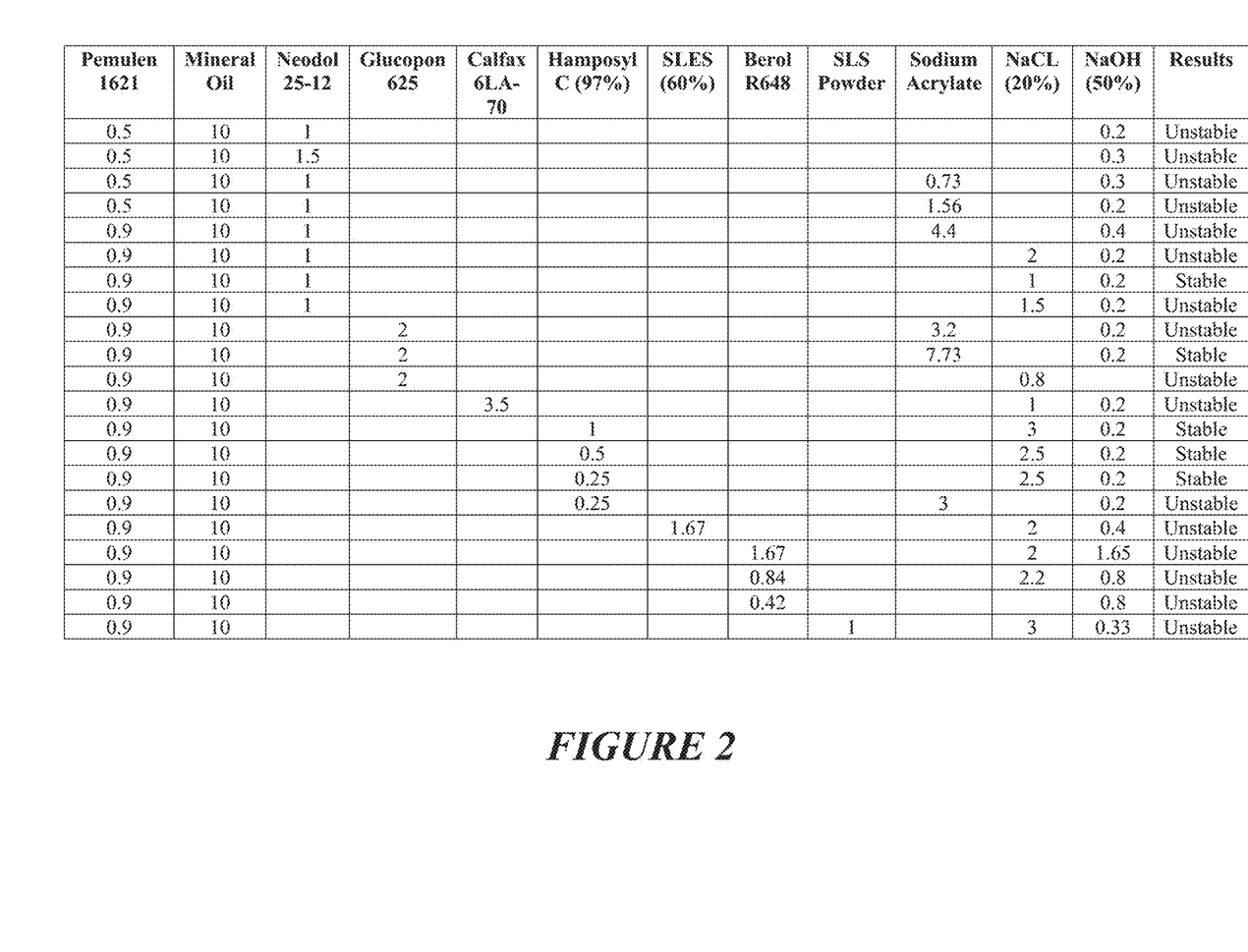

Pemulen 1621 was mixed with mineral oil, surfactant, water, and, if needed, sodium hydroxide for pH of seven and sodium chloride for viscosity, all according to FIG. 2.

Example 3

A premix was made comprising of fragrance or oil, polymer, Trilon M, carrageenan, and, in certain formulations surfactant, were combined. Using a stand mixer, blades were placed just above surface of the premix. Deionized water was slowly added while blades moving at 1000 rpm and mixing continued for 15 minutes. Sodium hydroxide was then added for pH of about seven, and mixing continued for 15 additional minutes. For the concentrates containing Tomamine Q-14-2 or Tomamine Q-C-15, the surfactant is added after pH of seven is achieved. The concentrate was then diluted 10 times with 11 grain water and visually assessed for droplet size and oil separation. The results formulations are provided in Table 9.

TABLE 9

Successful Surfactant Combinations with Pemulen 1621.

| | Test Formulations (wt. %) | | | | | | | | |
|---|---|---|---|---|---|---|---|---|---|
| | A | B | C | D | E | F | G | H | I |
| Pemulen 1622 | 0.45 | 0.45 | 0.45 | 0.45 | 0.45 | 0.45 | 0.45 | 0.45 | 0.45 |
| Fragrance | 5 | 5 | 5 | 5 | 5 | 5 | 5 | 5 | 5 |
| Trilon M | 0 | 0 | 0.5 | 0.5 | 0.5 | 0.5 | 0.5 | 0.5 | 0.5 |
| Carrageenan | 0.2 | 0.4 | 0 | 0 | 0 | 0 | 0 | 0 | 0 |
| Surfactant in pre-mix | Yes | Yes | Yes | Yes | Yes | No | No | No | No |
| Neodol 25-12 | 0.5 | 0.5 | 0.5 | 0 | 0 | 0 | 0 | 0 | 0 |
| Tomadol 25-7 | 0 | 0 | 0 | 0.5 | 0 | 0 | 0 | 0 | 0 |
| Neodol 91-6 | 0 | 0 | 0 | 0 | 0.5 | 0 | 0 | 0 | 0 |
| Tomadol 901 | 0 | 0 | 0 | 0 | 0 | 0.5 | 0 | 0 | 0 |
| Tomadol 902 | 0 | 0 | 0 | 0 | 0 | 0 | 0.5 | 0 | 0 |
| Tomamine AO-405 | 0 | 0 | 0 | 0 | 0 | 0 | 0 | 1 | 0 |
| Tomamine AO-455 | 0 | 0 | 0 | 0 | 0 | 0 | 0 | 0 | 1 |
| NaOH | 0.4 | 0.5 | 0.4 | 0.4 | 0.4 | 0.4 | 0.4 | 0.4 | 0.4 |

All of the test formulations in Table 9 provided excellent results, i.e., a stable, dilutable emulsion.

Pemulen 1622 was dispersed in oil, or fragrance, using a stand mixer with a medium shear blade at 300 rpm for three minutes. Zero-grain water, and Trilon M or carrageenan if required, was added and mixing continued at 1000 rpm for 15 minutes, and sodium hydroxide was added for pH control. Surfactant and any necessary salt solution to control viscosity were mixed in for another 10 minutes. Five grams of the concentrate was then diluted with 95 grams of either deionized or 10 grain water for three minutes at 800 rpm and visually assessed for droplet size and oil separation. The formulations are shown in Table 10.

TABLE 10

Successful Pemulen 1622 Solutions.

| | Test Formulations (wt. %) | | | | |
|---|---|---|---|---|---|
| | A | B | C | D | E |
| Pemulen 1622 | 0.03 | 0.03 | 0.03 | 0.03 | 0.03 |
| Neodol 25-12 | 0.05 | 0 | 0 | 0 | 0 |
| Tomadol 25-7 | 0 | 0.05 | 0 | 0 | 0 |
| Tomamine AO-405 | 0 | 0 | 0.1 | 0 | 0 |
| Tomamine AO-455 | 0 | 0 | 0 | 0.1 | 0 |
| Amphosol CA | 0 | 0 | 0 | 0 | 0.167 |
| Trilon M | 0 | 0 | 0 | 0.025 | 0.025 |
| Mineral Oil | 0 | 0.5 | 0.5 | 0 | 0.5 |
| Fragrance | 0 | 0 | 0.025 | 0.025 | 0.025 |
| Water (0 grain) | 4.61 | 4.61 | 4.59 | 4.59 | 4.494 |
| Water (10 grain) | 95 | 95 | 95 | 95 | 95 |
| NaOH | 0.01 | 0.01 | 0.01 | 0.01 | 0.01 |
| NaCl | 0.025 | 0.025 | 0 | 0 | 0.03 |

All of the formulations in Table 10 were diluted with 10 grain water and the emulsions remained stable and the diluted compositions retained flowable properties.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

The inventions being thus described, it will be obvious that the same may be varied in many ways. Such variations are not to be regarded as a departure from the spirit and scope of the inventions and all such modifications are intended to be included within the scope of the following claims. The above specification provides a description of the manufacture and use of the disclosed compositions and methods. Since many embodiments can be made without departing from the spirit and scope of the invention, the invention resides in the claims.

What is claimed is:

1. A composition comprising:
a carrier, an alkalizing agent, and an emulsion in the carrier, wherein the emulsion comprises a hydrophobic component and a surfactant and the carrier comprises water,
wherein the surfactant forms an interfacial film;
wherein the surfactant is present in a concentration between about 0.1 wt. % and about 1 wt. % of the composition, wherein the surfactant comprises a cross-linked copolymer of acrylic acid C10-C30 alkyl acrylate; and
wherein the surfactant has an HLB of at least about 6;
wherein the carrier is present in an amount between about 80 wt. % and about 98 wt. % of the composition;
wherein the hydrophobic component is in a concentration between about 0.1 wt. % and about 5 wt. % and comprises an oil;
wherein the oil comprises mineral oil;
between about 0.01 wt. % and about 5 wt. % of the alkalizing agent;
wherein the emulsion encapsulates a fragrance, a dye, or a mixture thereof; and
wherein the emulsion is stable at temperatures between about 10° C. and about 40° C. and stable for 24 hours upon dilution within the composition.

2. The composition of claim 1, wherein the surfactant has an HLB of at least about 8.

3. The composition of claim 2, wherein the emulsion further comprises a salt in a concentration of between about 0.01 wt. % and about 1 wt. %.

4. The composition of claim 1, wherein the emulsion is diluted within the composition at a weight ratio between about 1:2 and about 1:25 of emulsion to carrier.

5. The composition of claim 1, wherein the emulsion further comprises a chelating agent, a thickener, an additional surfactant, or a mixture thereof.

6. A composition comprising:
a carrier and an emulsion in the carrier;
wherein the emulsion comprises a hydrophobic component, a surfactant, an alkalizing agent, and a salt;
wherein the carrier comprises water, a solvent, or a mixture thereof;
wherein the surfactant forms an interfacial film;
wherein the surfactant is present in a concentration between about 0.1 wt. % and about 1 wt. % of the composition, and wherein the surfactant comprises a cross-linked copolymer of acrylic acid C10-C30 alkyl acrylate;
wherein the hydrophobic component is in a concentration between about 0.1 wt. % and about 5 wt. % and comprises an oil;
wherein the oil comprises mineral oil;
wherein the alkalizing agent is in a concentration of between about 0.01 wt. % and about 5 wt. %;
wherein the carrier is present in an amount between about 80 wt. % and about 98 wt. % of the composition;
wherein the surfactant has an HLB of at least about 7;
wherein the emulsion encapsulates a fragrance, a dye, or a mixture thereof;
wherein the emulsion is stable at temperatures between about 10° C. and about 40° C. and stable for 24 hours upon dilution within the composition.

7. The composition of claim 6, wherein the composition is diluted with a second carrier at a weight ratio between about 1:2 and about 1:25 of emulsion to second carrier and the total concentration of the carrier of the composition and the second carrier is between about 95 wt. % and about 98 wt. %.

8. The composition of claim 7, wherein the surfactant has a concentration between about 0.1 wt. % and about 0.5 wt. %.

9. The composition of claim 6, wherein the surfactant has an HLB of between about 8 and about 12.

10. The composition of claim 9, wherein the alkalizing agent is an alkali metal hydroxide; and wherein the salt is a chloride salt.

11. The composition of claim 6, wherein the emulsion further comprises a chelating agent, a thickener, an additional surfactant, or a mixture thereof; and
wherein the emulsion further encapsulates an oil, an encapsulated surfactant, water, or a mixture thereof.

12. A method of diluting the composition of claim 1 comprising:
obtaining the composition of claim 1;
diluting the composition with a second carrier to form a diluted composition;
wherein the second carrier is water, a solvent, or a mixture thereof;
wherein the composition is diluted at a ratio of emulsion to the second carrier of between about 1:2 and about 1:25;
wherein upon dilution the surfactant has a concentration of between about 0.1 wt. % and about 0.5 wt. % of the diluted composition;
wherein the concentration of the carrier of the composition of claim 1 and the second carrier is between about 95 wt. % and about 99 wt. %;
wherein the emulsion in the diluted composition is stable at temperatures between about 10° C. and about 40° C. and for at least 24 hours.

13. The method of claim 12, wherein the surfactant has an HLB of at least about 8.

14. The method of claim 12, wherein the emulsion further comprises a chelating agent, a salt, a thickener, an additional surfactant, or a mixture thereof; and
wherein the emulsion further encapsulates an encapsulated surfactant, water, or a mixture thereof.

15. The method of claim 12, wherein the emulsion in the diluted composition remains stable for at least 48 hours.

* * * * *